(12) United States Patent
Beaven (10) Patent No.: US 10,238,424 B2
(45) Date of Patent: Mar. 26, 2019

(54) OBSTETRIC APPARATUS AND METHOD

(71) Applicant: Modern Surgical Solutions, LLC, Covington, KY (US)

(72) Inventor: Richard B. Beaven, Covington, KY (US)

(73) Assignee: MODERN SURGICAL SOLUTIONS LLC, Covington, KY (US)

( * ) Notice: Subject to any disclaimer, the term of this patent is extended or adjusted under 35 U.S.C. 154(b) by 49 days.

(21) Appl. No.: 15/411,107

(22) Filed: Jan. 20, 2017

(65) Prior Publication Data

US 2018/0206886 A1 Jul. 26, 2018

(51) Int. Cl.
*A61B 17/44* (2006.01)
*A61B 17/00* (2006.01)
*A61B 90/00* (2016.01)

(52) U.S. Cl.
CPC .... *A61B 17/442* (2013.01); *A61B 2017/0023* (2013.01); *A61B 2017/0046* (2013.01);
(Continued)

(58) Field of Classification Search
CPC ........ A61B 17/442; A61B 2017/00557; A61B 2017/447; A61B 2017/445; A61B 2017/306; A61B 2017/308; A61B 17/22031; A61B 17/22032; A61B 17/42; A61B 17/44; A61B 2017/00287; A61B 2090/064; A61B 17/50; A61B 2017/00022; A61B 2017/00429; A61B 2017/00473; A61B 2017/00946; A61B 2017/22037; A61B 42/00; A61B 5/02411; A61B 17/12099; A61B 17/12136; A61B 2017/00132; A61B 2017/00221; A61B 2017/00849; A61B 2017/22034; A61B 2034/102; A61B 2090/032; A61B 2090/0814; A61B 2503/02; A61B 34/20; A61B 5/0011; A61B 5/0205; A61B 5/0448; A61B 5/14542; A61B 5/146;
(Continued)

(56) References Cited

U.S. PATENT DOCUMENTS 3,765,408 A * 10/1973 Kawai ................. A61B 17/442
606/123
8,556,913 B2 * 10/2013 Varma ................. A61B 17/442
606/122

(Continued)

*Primary Examiner* — Todd J Scherbel
*Assistant Examiner* — Andrew P. Restaino
(74) *Attorney, Agent, or Firm* — Ronald J. Richter; Hasse & Nesbitt LLC (57) ABSTRACT

An obstetric apparatus and method for repositioning a fetal head within the birth canal of a woman in labor. A user, typically an obstetrician, surgeon or similarly trained medical personnel, can efficiently and safely engage a fetal head that is wedged in the parturient woman's pelvis and lift it up in the birth canal towards the uterus, for safe delivery of the baby via C-section. The apparatus comprises an elongated and substantially rigid shaft, a pivoting neck and a soft engaging portion that includes a flexible outer cup and an inflatable inner cup for engaging the fetal head. The inventive apparatus and method can provide a mechanical advantage for repositioning the head of the fetus, and can provide assistance for C-section delivery in order to minimize maternal and neonatal complications.

12 Claims, 7 Drawing Sheets

(52) U.S. Cl.
CPC ............... *A61B 2017/00526* (2013.01); *A61B 2017/00557* (2013.01); *A61B 2017/445* (2013.01); *A61B 2017/447* (2013.01); *A61B 2090/061* (2016.02); *A61B 2090/065* (2016.02); *A61B 2090/0807* (2016.02)

(58) Field of Classification Search
CPC ...... A61B 5/6843; A61B 8/02; B25J 15/0023; B25B 9/00; B65G 47/908; A61F 13/2045; A61M 2210/1475
USPC ........................................................ 606/122
See application file for complete search history.

(56) References Cited

U.S. PATENT DOCUMENTS

| | | | |
|---|---|---|---|
| 9,039,714 B2* | 5/2015 | Barrier | A61B 17/442 606/122 |
| 9,247,958 B2* | 2/2016 | Odon | A61B 17/22032 |
| 9,408,633 B2* | 8/2016 | Leitch | A61B 17/42 |
| 2013/0158563 A1 | 6/2013 | Adams | |
| 2013/0304081 A1* | 11/2013 | George | A61B 17/442 606/123 |

* cited by examiner

OBSTETRIC APPARATUS AND METHOD

FIELD OF THE INVENTION

The present invention relates generally to the field of obstetrics and particularly to an obstetric apparatus for repositioning a fetal head within a birth canal.

BACKGROUND OF THE INVENTION

Cesarean section, commonly referred to as a C-section, is a surgical procedure that provides an alternative to difficult or failed vaginal delivery of a baby, and entails delivery through a surgical incision in the parturient woman's abdomen and uterus. In recent years a significant proportion of deliveries via C-section have been performed during the second or later stages of labor. Since the pregnant woman has labored for a period of time, the fetal head may be well seated in the maternal pelvis. At such a late stage, molding and caput of the baby's head occurs in an attempt to squeeze the head through the sometimes narrow and tortuous route of the maternal birth canal. The tissues of the vagina and cervix can stick to the baby's head in this very wet environment, creating an environment which places a large amount of suction on the fetal head. This environment can create significant resistance to the obstetrician's attempts at digital or manual extraction. As a result, the obstetric surgeon will often encounter a difficult and potentially traumatic disengagement of the deeply wedged fetal head during the ensuing C-section procedure.

The maneuvers to disengage the impacted fetal head (IFH) include pushing the head back up through the birth canal and into the uterus, and/or pulling the infant's feet up through the uterine incision. Both methods may cause serious maternal and neonatal complications. For example, a surgical assistant will typically place a hand into the vagina and push up on the fetal head while the surgeon attempts to gain leverage from the surgical field above. Often when the seal is broken a loud sucking sound can be heard as the head disengages from the birth canal walls. The force required to accomplish this may at times be excessive, and may lead to complications such as low neonatal Apgar scores, fetal injuries such as clavicle fracture, long-bone fractures or skull depression/fracture, fetal head laceration, tearing and extension of the uterine incision, maternal hemorrhage, injury to the maternal bladder or uterine blood vessels, and (rarely) fetal death.

A deeply impacted fetal head is estimated to occur during 1.5% of all C-section deliveries and 25% of all emergency C-sections. With less training in forceps deliveries and recent recommendations by the American College of Obstetricians and Gynecologists (ACOG) and other sources to continue pushing during the second stage of labor for up to three hours, the problem of an IFH is quickly becoming a growing problem. In addition, maternal obesity, diabetes and macrosomia continue to contribute to the incidence of IFH requiring emergency C-section.

Devices and methods have been proposed for assisting delivery via C-section when the fetal head is deeply wedged in the female pelvic cavity. For example, U.S. Pat. No. 9,055,973 and U.S. Pat. No. 8,556,913, both to Varma disclose an inflatable balloon attached to one side of a foldable plate for supporting and pushing an impacted fetal head up into the uterus. While useful, the plate can wedge itself into the vaginal sidewalls which can be damaging to the edematous tissues and cause lacerations. U.S. Pat. No. 9,408,633 to Leitch teaches a fetal head support for elevating an impacted fetal back into the uterus. The contact surface of the support includes gaps which do not contact the fetal head, such that the device applies pressure unevenly to the fetal skull. U.S. Pat. No. 9,039,714 to Barrier et al. discloses an obstetric device which expels air to break the vacuum seal between the fetal head and the birth canal walls. The device is not intended for supporting or relocating the fetal head within the birth canal.

While the above prior art devices and methods may be useful for their intended purpose, there remains a need for an improved apparatus for repositioning an impacted fetal head and guiding it back up through the birth canal and into the uterus prior to delivery by C-section. It would also be beneficial to provide a more efficient means for displacing an impacted fetal head that will minimize maternal and neonatal complications.

SUMMARY OF THE INVENTION

In light of the above, the present invention provides an obstetric device and method for efficiently and gently repositioning an impacted fetal head prior to delivery by C-section, while minimizing maternal and neonatal complications.

One aspect of the invention provides an obstetric apparatus, comprising: (a) a substantially rigid and non-collapsible shaft having a proximal end and a distal end, the shaft defining a lumen running longitudinally through the length thereof, the lumen including an opening at the proximal end of the shaft for receiving a fluid, the shaft comprising a handle portion at the proximal end for grasping by a user and a body portion at the distal end, the body portion being curved to approximate the natural curvature of a parturient woman's birth canal; (b) an engaging portion for engaging a fetal head in a parturient woman's birth canal, the engaging portion comprising an outer cup reversibly deformable between a compact position and an expanded position; and an inflatable inner cup for inflation by a user, wherein the inflatable inner cup is in fluid communication with the lumen of the shaft and comprises a distal contact surface including a central concave indentation; and (c) a pivoting neck connecting the distal end of the shaft to the outer cup and providing a pivoting motion for the engaging portion, wherein the apparatus is useful for repositioning the fetal head towards the uterus.

Another aspect of the invention provides an obstetric apparatus for repositioning a fetal head wedged in a parturient woman's birth canal, the apparatus comprising: (a) a substantially rigid and non-collapsible shaft having a proximal end and a distal end, the shaft comprising: (i) a lumen running longitudinally through the length of the shaft, the lumen comprising an opening at the proximal end of the shaft for receiving a fluid; (ii) a handle portion at the proximal end for grasping by a user; (iii) a body portion at the distal end, the body portion being curved to approximate the natural curvature of a parturient woman's birth canal; and (iv) a pressure gauge for both indicating and buffering the pressure applied by the user to a fetal head wedged in the parturient woman's birth canal; (b) an engaging portion for engaging the fetal head, the engaging portion comprising: (i) a flexible outer cup reversibly deformable between a compact position and an expanded position, the outer cup being biased to assume the expanded position; and (ii) an inflatable inner cup, the inner cup comprising a distal contact surface including a central concave indentation for engaging and molding to the head, wherein the inflatable inner cup is in fluid communication with the lumen of the shaft for inflation by the user; and (c) a pivoting neck connecting the distal end of the shaft to the engaging portion and providing a pivoting motion for the engaging portion.

Another aspect of the invention provides a method of repositioning the head of a fetus within a parturient woman's birth canal, the method comprising the steps of: (a) inserting an obstetric apparatus into a birth canal of a parturient woman, the obstetric apparatus comprising: (i) a substantially rigid and non-collapsible shaft including a proximal end and a distal end, the shaft defining a lumen running longitudinally through the length thereof, the lumen including an opening at the proximal end of the shaft for receiving a fluid, the shaft comprising a handle portion at the proximal end for grasping by a user and a curved body portion at the distal end; (ii) an engaging portion for engaging a fetal head located in the birth canal, the engaging portion comprising an outer cup and an inflatable inner cup, the inner cup in fluid communication with the lumen of the shaft and comprising a contact surface including a central concave indentation for engaging and molding to the fetal head; and (iii) a pivoting neck connecting the shaft to the outer cup and providing a pivoting motion for the engaging portion; (b) positioning the engaging portion of the obstetric apparatus adjacent the fetal head; (c) injecting fluid into the opening at the proximal end of the shaft to inflate the inflatable inner cup of the engaging portion; (d) applying pressure along the shaft so that the contact surface of the inflatable inner cup engages the fetal head and transfers the applied pressure to the fetal head; and (e) maneuvering the shaft to reposition the fetal head towards the uterus of the parturient woman.

The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1A:
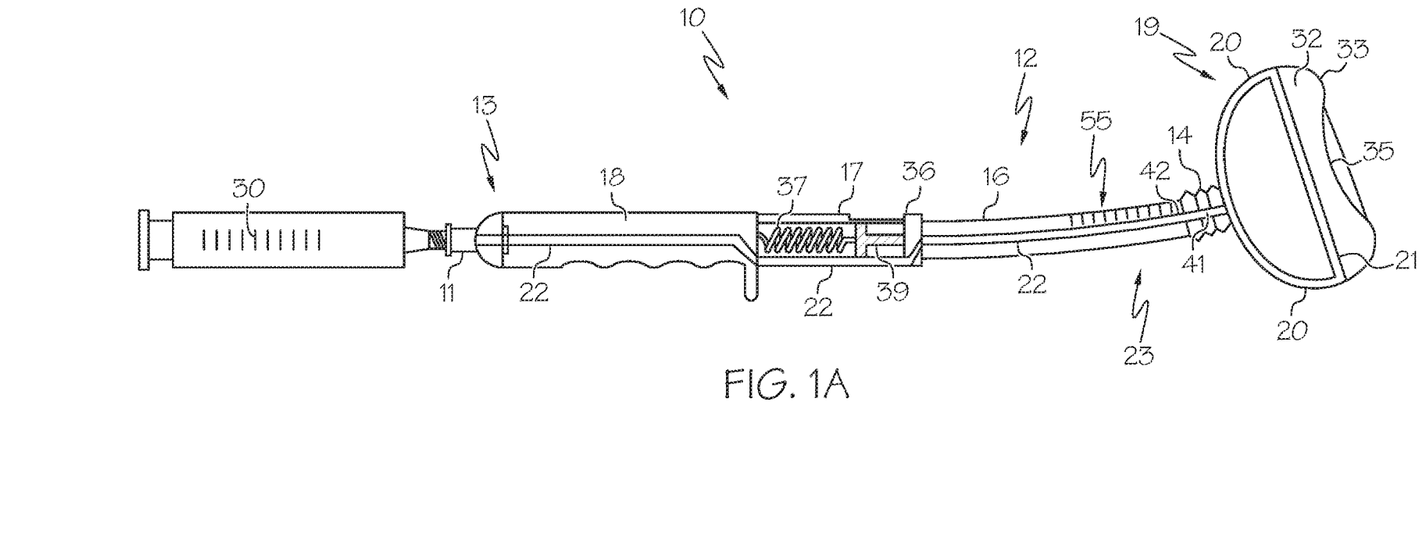
FIG. 1A is a side cross-sectional view depicting one embodiment of the inventive apparatus for displacing a fetal head.
Figure 1B:
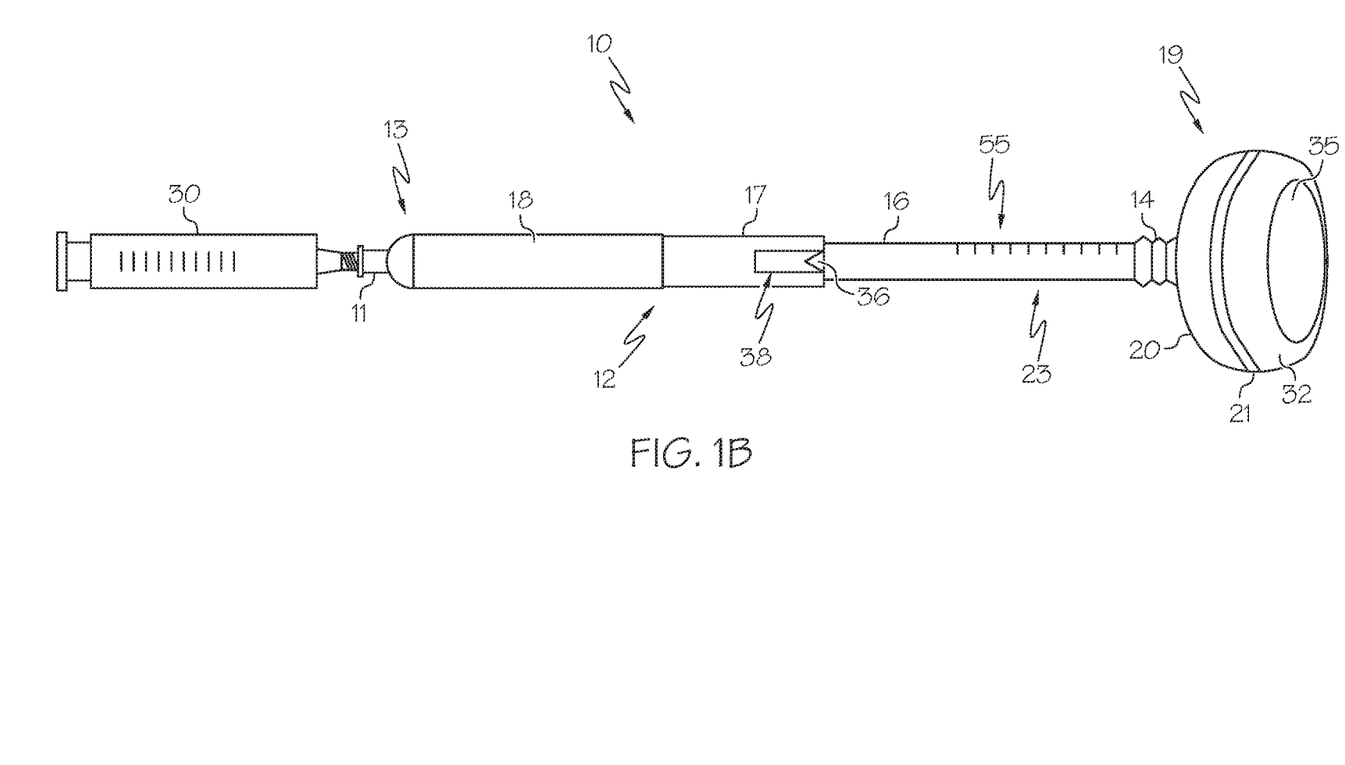
FIG. 1B is a top view of the apparatus of FIG. 1.

FIG. 1A and FIG. 1B illustrate an improved apparatus for repositioning a fetal head wedged in a parturient woman's birth canal, wherein a user, typically an obstetric physician, surgeon or similarly trained clinician or medical personnel, can efficiently and safely engage a fetal head presently wedged in the birth canal of the parturient woman's pelvis and reposition it back towards the uterus. As illustrated, the inventive apparatus 10 can comprise an elongated, substantially rigid and non-collapsible shaft 12, a pivoting neck 14, and an engaging portion 19 for engaging the head of the fetus. The pivoting neck 14 connects the distal end 23 of the shaft to the engaging portion 19, providing a pivoting motion for the apparatus. The proximal end 13 of the shaft 12 includes a substantially straight handle portion 18 for grasping by the user. A pressure gauge 17 is included between the handle 18 at the proximal end, and a curved body portion 16 at the distal end. The pressure gauge 17 can indicate the amount of pressure being applied to the fetal head and also buffer the initial force applied to the fetal head by the user.

As illustrated in FIGS. 1A and 1B, the shaft includes a curved body portion 16 connected to the engaging portion 19 by way of the pivoting neck 14. A distance indicator such as graduated markings 55 can be included on the body 16 to indicate the distance traveled by the engaging portion 19 from the vaginal introitus to the fetal head within the birth canal. The body portion 16 is typically curved in comparison to the handle 18, as best seen in FIG. 1A, such that when the apparatus 10 is properly positioned this curvature approximates the natural curvature of the birth canal. The body portion 16 should be long enough to extend from the pivoting neck 14 adjacent the fetal head, through the birth canal and out of the vaginal opening to the external environment, so that graduated markings 55 and the pressure indicator 36 of the pressure gauge 17 are visible, and the handle 18 of the shaft is accessible for manipulation and later removal of the apparatus by the user.

Looking at the cross-sectional side view of FIG. 1A, a syringe 30 can be connected to a proximal opening 11 in the proximal end 13 of the shaft 12. The shaft 12 includes an internal lumen 22 extending longitudinally through its length. At the distal end 23 of the shaft the lumen 22 ends at a distal opening 42, which is in fluid communication with an orifice tubing 41 of the inflatable inner cup 32. The orifice tubing 41 is typically continuous with (i.e. part of) and in fluid communication with the inflatable inner cup 32. The proximal opening 11 can be a luer lock fitting, as illustrated, or other fluid-competent connector for receiving the syringe 30. The distal opening 42 can also be a fluid-competent connector, as is known in the art.

Figure 2:
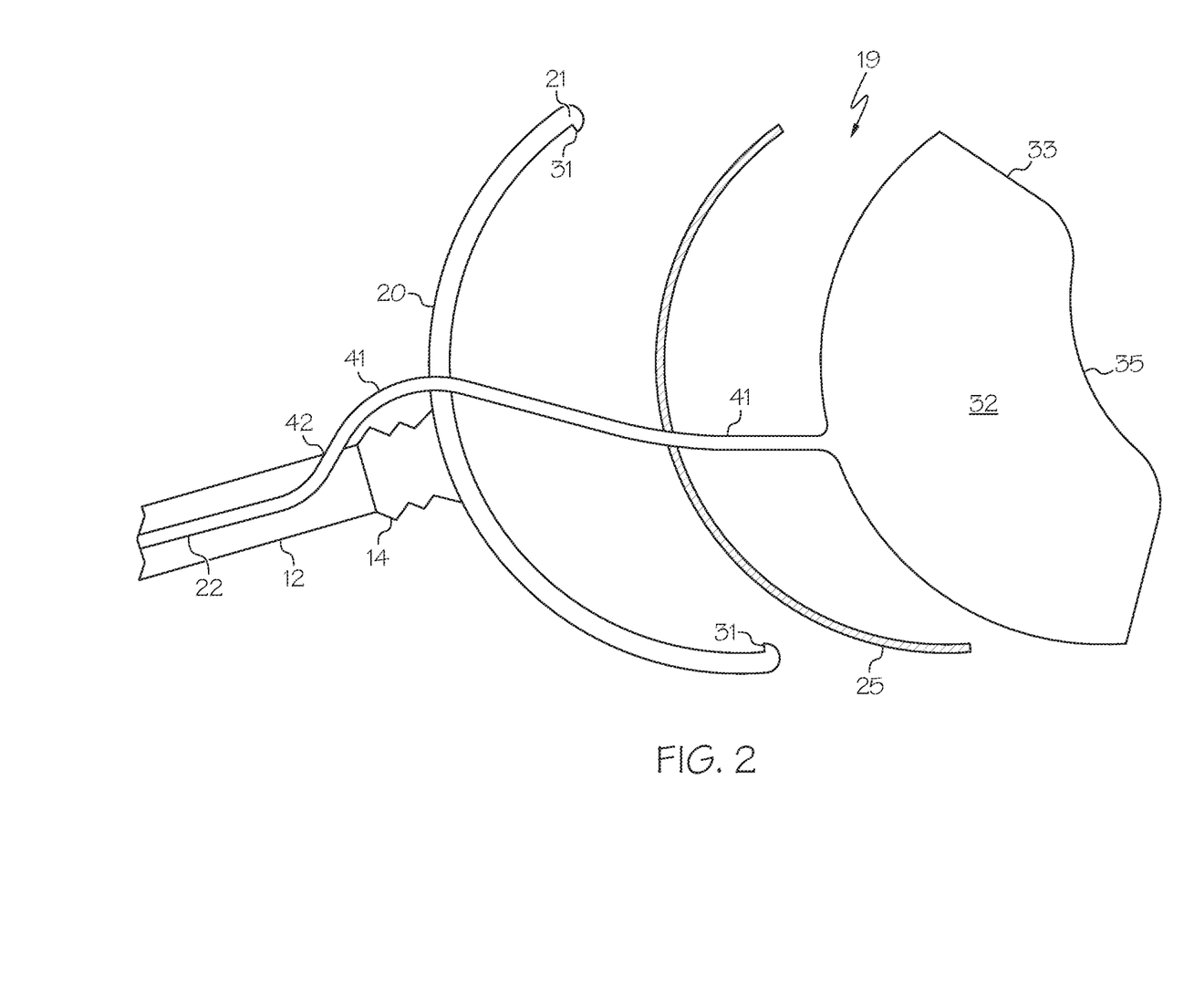
FIG. 2 is an exploded cross-sectional side view of the engaging portion of one embodiment of the inventive apparatus.
Figure 3A:
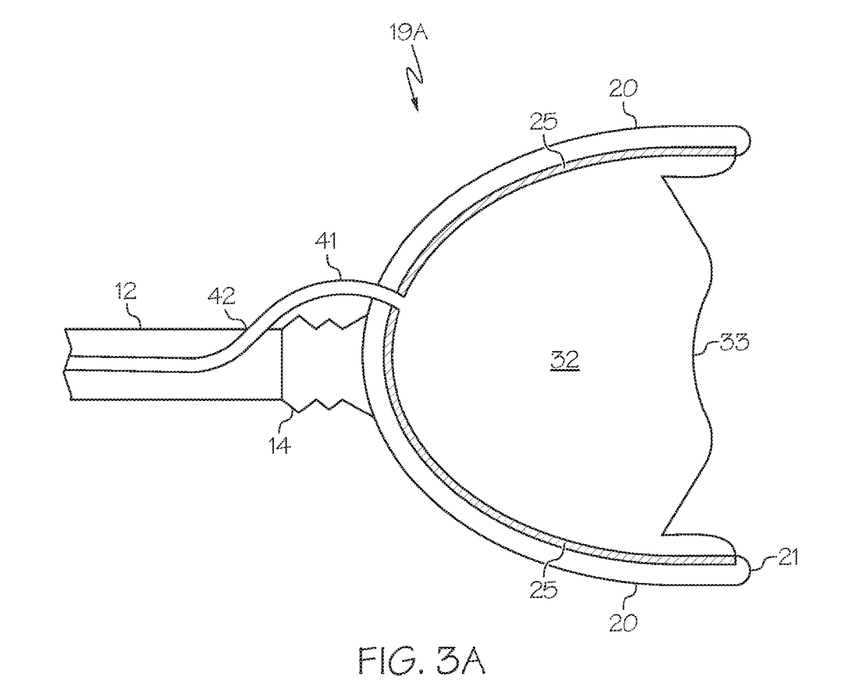
FIG. 3A is a side cross-sectional view of the apparatus of FIG. 2 in a compact position.
Figure 3B:
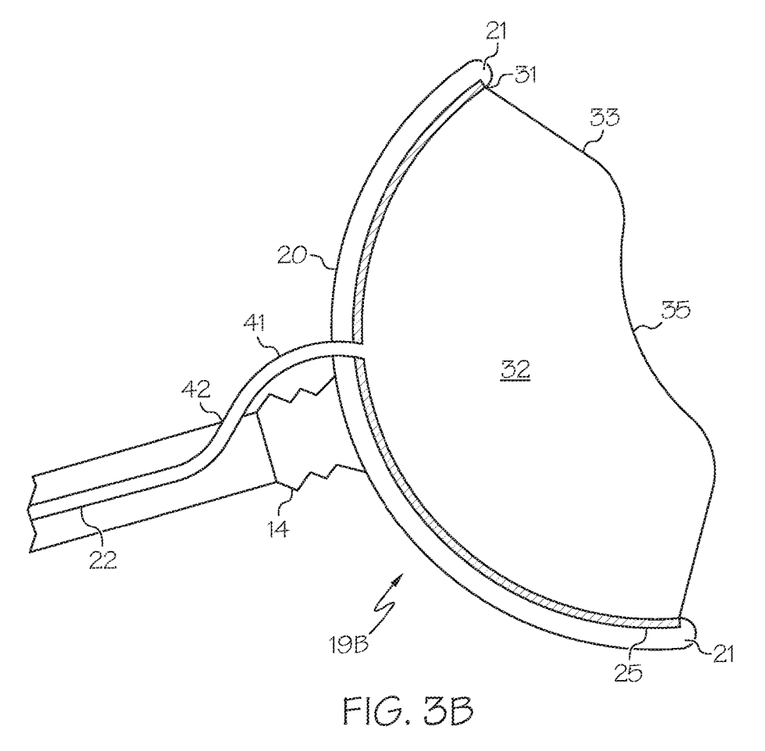
FIG. 3B is a side cross-sectional view of the apparatus of FIG. 2 in an expanded position.

The engaging portion 19 includes a flexible outer cup 20 and the inflatable inner cup 32. A soft base portion 25 is preferably included on the inner surface of the outer cup 20, as best illustrated in FIGS. 2, 3A and 3B. The base 25 can be made of a very soft material such as foam rubber or other cellular or sponge type of polymeric foam. The base 25 adds cushioning to the fetal head should the applied pressure cause the head to come into contact with it during use. The inflatable inner cup 32 is operable to engage the head of the fetus, which can be impacted or wedged within the parturient woman's birth canal. The inner cup 32 includes a distal surface 33 which comes into contact with the fetal head. The contact surface 33 is typically constructed to include a central concave indentation 35 which, when the inner cup is inflated, is substantially complementary to the shape of the vertex of a fetal head.

To inflate the inner cup 32, a user can inject fluid such as air or saline from a 10 cc to 60 cc syringe, 30 connected to the proximal opening 11 the shaft 12, such that fluid injected at the proximal opening 11 will pass through the lumen 22 and orifice tubing 41 to expand and/or inflate the inner cup 32. Once the inner cup 32 is inflated, the proximal opening 11 can be locked and the syringe 30 can be removed, with the inner cup remaining in that particular inflated position until further inflation or deflation is desired by the user as needed, either for adjustment during use or prior to removal. For example, once the inner cup is placed adjacent the fetal head and inflated to engage or otherwise make contact with the head, the user can further inflate or deflate the inner cup as deemed necessary by the user in order to shape or mold the contact surface 33 of the cup 32 to the shape of the fetal head, or to release any suction or vacuum that may have developed between the concave contact surface 33 and the fetal head.

The inflatable inner cup 32 is preferably made of a material which during use can be inflated or deflated as necessary so that the contact surface 33 and its concave indentation 35 can further shape or mold to the shape presented by the fetal head within the birth canal. In contrast to similar prior art devices which are susceptible to creating pressure points and uneven pressure distribution onto the fragile fetal skull, the molding feature provided by the concave contact surface 33 allows the upward cephalic pressure exerted by the user to be equally distributed along the surface area available for making direct contact with the fetal head. This molding feature provides a smoother and more gentle transmission of the applied pressure to the presenting surface of the fetal head, and substantially eliminates the possibility of pressure point trauma. After repositioning is complete, the inner cup 32 can be inflated or deflated as necessary prior to removal, to release any suction or vacuum that may have developed with the fetal head.

As shown in FIGS. 1A and 1B, a pressure gauge 17 can be included on the shaft 12 to both measure the applied pressure and to act as a shock absorber to cushion the energy transferred from the handle 18 to the fetal head. An abrupt increase in pressure to the fetal head is known to result in a decrease in fetal heart rate (vagal response), often necessitating a hurried and emergent Cesarean delivery in a less controlled manner. After a prolonged labor and hours of unsuccessful pushing the fetus is commonly in some degree of distress already. Buffering the pressure applied to the fetal head would mitigate such risk, which is an improvement over similar prior art devices. As shown in FIG. 1A, the pressure gauge 17 can be in the form of a pneumatic air cylinder having a piston 39 and a coil spring 37. The spring 37 and the piston 39 can initially resist or absorb any applied pressure from being directly transferred from the handle 18 to the engaging portion 19. That is, as the engaging portion 19 pushes against the fetal head, the coil spring 37 will initially compress and absorb the load pushing back from the fetal head, reducing the risk of trauma to the fetal head. Also, as the spring 37 is compressed there can be movement of a pressure indicator 36 (which can be continuous with, i.e. part of, the body portion 16) towards the handle 18. The length/degree of movement of the pressure indicator 36 towards the handle 18 can be calibrated to provide a reading 38 (see FIG. 1B) of the amount of pressure being applied to the fetal head. While the pressure gauge 17 illustrated in FIGS. 1A and 1B is a spring-loaded pneumatic pressure gauge, other known gauges may be used, so long as they can provide pressure information while also buffering the force applied by the user to the fetal head.

FIG. 2 illustrates an expanded cross-sectional view of the engaging portion 19 of the apparatus, and FIGS. 3A and 3B illustrate that the outer cup 20 (and thus the engaging portion 19) is reversibly deformable between a compact position 19A (FIG. 3A) and an expanded position 19B (FIG. 3B). As can be appreciated by viewing these figures, the outer cup 20 can provide structural support for the substantially non-rigid inflatable inner cup 32, and can include a rim 21. The outer cup 20 is manufactured to be flexible yet firm enough to bias itself and thus the engaging portion 19 to the expanded position 19B. The rim 21 of the outer cup is reversibly collapsible, ring-shaped and slightly thicker than the rest of the cup 20, and when compressed will tend to open back out to its ring shape when released. This, along with the cup shape of the outer cup, biases the outer cup to return to the expanded position 19B when not being actively compressed. As best seen in FIG. 2, the rim 21 can include an inner ridge 31 which can aid in attaching the inflatable inner cup 32 to the outer cup 20. The inner ridge 31 can serve to position the inner cup properly within the outer cup, anchoring the inner cup so that the contact surface 33 of the inner cup is exposed to the fetal head when the outer cup 20 is in the expanded position 19B. The rim 21 is preferably rounded on its outer edges so that it is non-traumatic to the typically edematous vaginal and cervical tissues of the birth canal. The rim 21 and inner ridge are typically continuous with the outer cup 20 and made of the same material, such as silicone rubber or other biocompatible elastomer.

Looking at FIG. 2, the lumen 22 is in fluid communication with the orifice tubing 41 of the inflatable inner cup 32 at the distal opening 42 of the shaft 12. From the distal opening 42, the orifice tubing 41 passes external to the pivoting neck 14 and through the outer cup 20 and foam rubber base 25 to join the inner cup 32. The tubing 41 is in fluid communication with, and typically joins or becomes part of, the inner cup 32. Regarding the openings 11, 42 of the shaft 12, in FIG. 1 the proximal and distal openings 11, 42 are located at their respective ends 13, 23 of the shaft 12 so that the lumen 22 exits the shaft 12 in a longitudinal direction relative to the axis of the shaft, but other locations for the openings 11, 42 may also be envisioned, as illustrated by the side location of the distal opening 42 in FIGS. 2, 3A and 3B.

The orifice tubing 41 can either be internalized in the pivoting neck 14, as illustrated in FIG. 1, or the tubing 41 can pass externally to the pivoting neck 14 to avoid being pinched, as illustrated in FIGS. 2, 3A/B. If external to the neck 14, a protective sheath (not shown) can be used to envelope and protect the tubing 41 from being snagged or otherwise interfering with the fetus. Indeed, it is contemplated that an elongated envelope of a flexible plastic sheet material such as polyethylene can be placed over the external tubing or even over the portions of the apparatus which are inserted into the birth canal during use, in order to protect the device and minimize contact with bodily fluids. Such protective sheaths are known in the art, as disclosed, e.g., in Suzuki U.S. Pat. No. 7,833,202, the contents of which are incorporated herein by reference.

A user can place the outer cup 20 into the compact position 19A (as illustrated in FIG. 3A) prior to insertion through the vaginal introitus of the parturient woman. For example, the outer cup 20 (as well as the base 25 and inner cup 32) of the engaging portion 19 can be manually caused by the user to reversibly collapse inwards towards the axis of the shaft 12 during insertion (position 19A). Once inserted past the vaginal introitus, the flexible outer cup 20 will spring or expand out (as much as permitted by the surrounding birth canal walls) to the expanded position 19B, and is now in position for inflation of the inner cup 32. The flexible and self-expanding properties of the outer cup 20 help the user insert the apparatus effectively but with a minimum of risk or discomfort for the mother. The flexibility of the outer cup 20 combined with its self-expansion properties can also serve to gently stretch or expand the walls of the birth canal that surround the wedged fetal head, without damaging or causing any trauma to the edematous maternal tissues, helping to release any vacuum or seal developed during labor between the fetal head and the birth canal walls.

Figure 4:
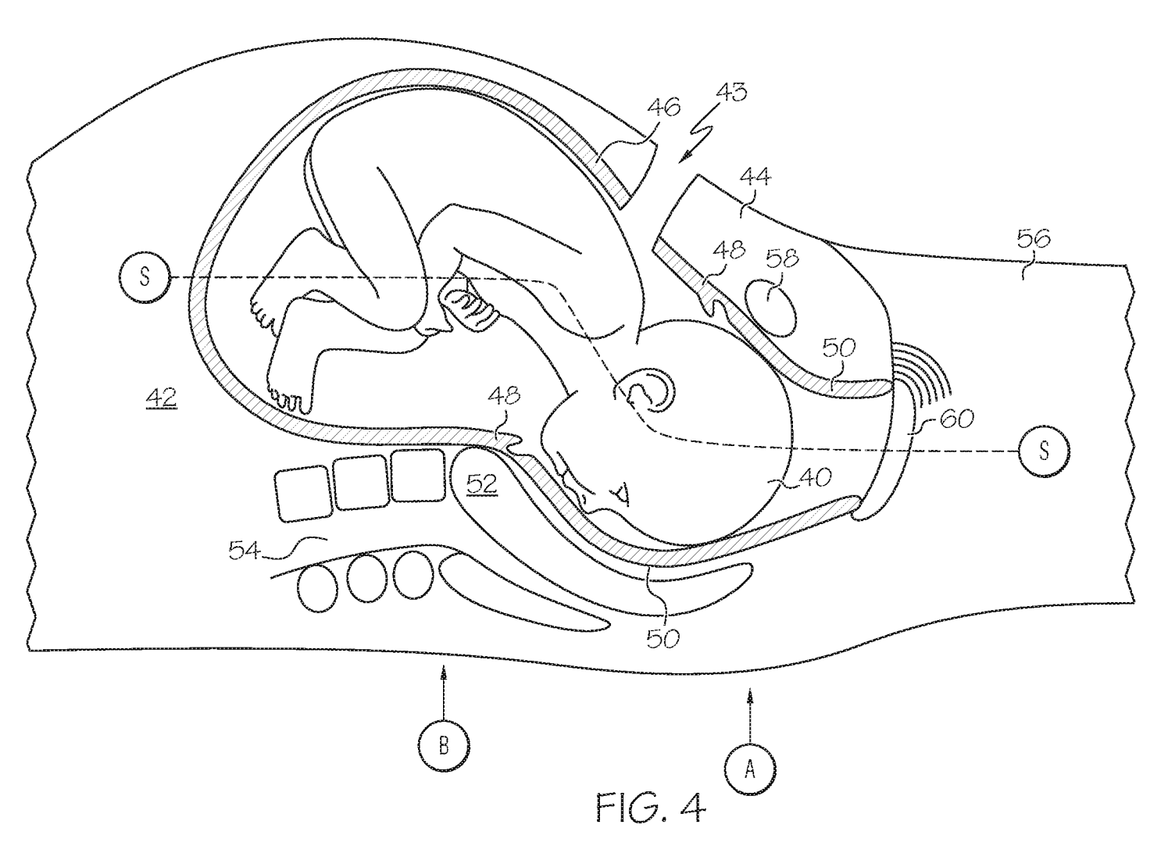
FIG. 4 illustrates an impacted fetal head in the uterus of a pregnant woman.

FIG. 4 illustrates an impacted fetal head 40 wedged in the birth canal of the parturient woman 42. At this point during labor, the cervix is typically in a fully dilated and thinned out state (full effacement), such that the cervical walls 48 are generally continuous and indistinguishable with the surrounding vaginal walls 50. Following prolonged pushing, the fetal head 40 will have traveled well past the cervical os and become wedged between the pubic bone 58 and sacral promontory 52 in the vaginal portion 50 of the birth canal. The surgeon performing the C-section procedure will typically make an incision 43 through both the abdominal wall 44 and uterine wall 46 for delivery of the neonate therethrough. Typically, when the surgeon opens the uterus, the shoulder of the fetus can be seen. This is called "the shoulder sign" when there is an impaction. The skin incision is typically made a few centimeters above the pubic bone 58. The uterine wall 46 is shown here continuous with the birth canal which includes the cervical walls 48 and the vaginal walls 50. The parturient woman's spine 54, leg 56, and vaginal introitis 60 are also illustrated for orientation and understanding of the position of the baby's head 40 when impacted in the birth canal.

As shown in FIG. 4, the path of the birth canal is an "S" curve which is dictated by the sacral promontory 52 and pubic bone 58 of the pelvis. Position A illustrates a typical location of the impacted head 40 in the birth canal, and position B is the desired position to where the head 40 should be lifted by the obstetrician for safe and successful delivery through uterine incision 43. The present invention is intended for assisting the surgeon to reposition the impacted fetal head 40 located at position A and to gently lift or move it back up along the curve of the birth canal "S" to position B. If the diagnosis of impacted fetal head (IFH) was made pre-operatively or if the obstetrician believes using the device will aid with the C-section procedure, the engaging portion 19 can be placed within the birth canal prior to the procedure; alternatively, if the diagnosis of IFH was not anticipated then the device can be placed after the C-section procedure has begun. Once the compact engaging portion 19A (see FIG. 3A) is inserted past the vaginal introitis 60 (see FIG. 4), it will be biased to open to its expanded state 19B (see FIG. 3B). Once past the vaginal introitis, the expanding engaging portion 19 exposes the distal contact surface 33 of the inner cup 32 for engaging the fetal head via inflation by the user.

Figure 5A:
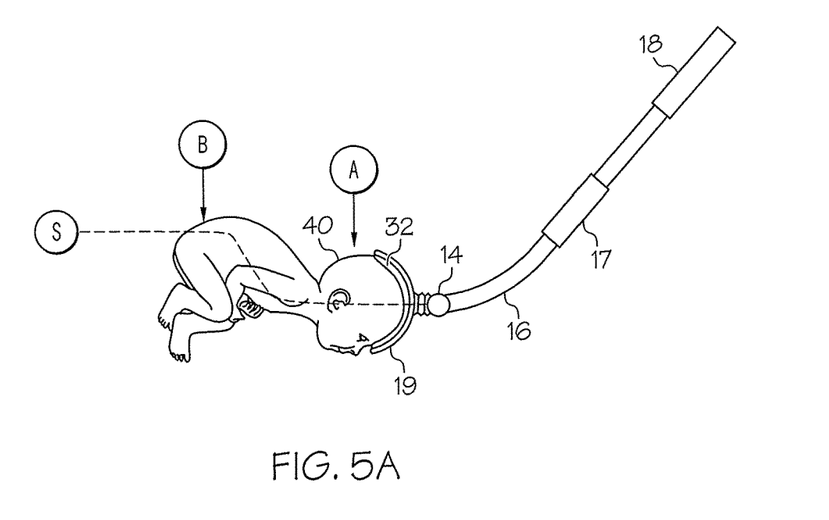
FIGS. 5A-5C illustrate stages of a general embodiment of the inventive apparatus as it repositions a fetal head along an "S" shaped pathway towards the uterus.
Figure 5B:
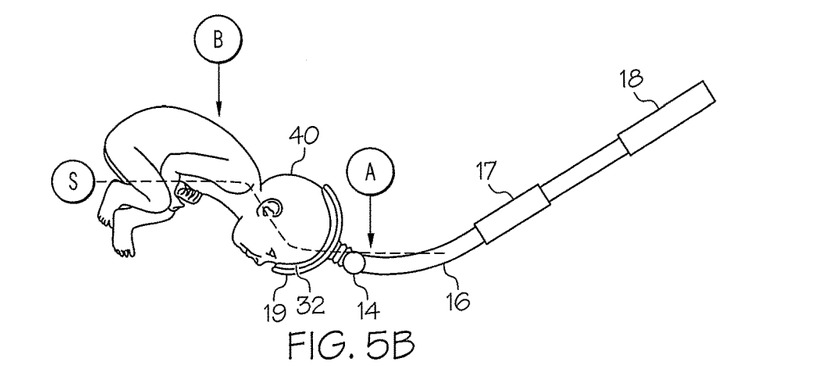
Figure 5C:
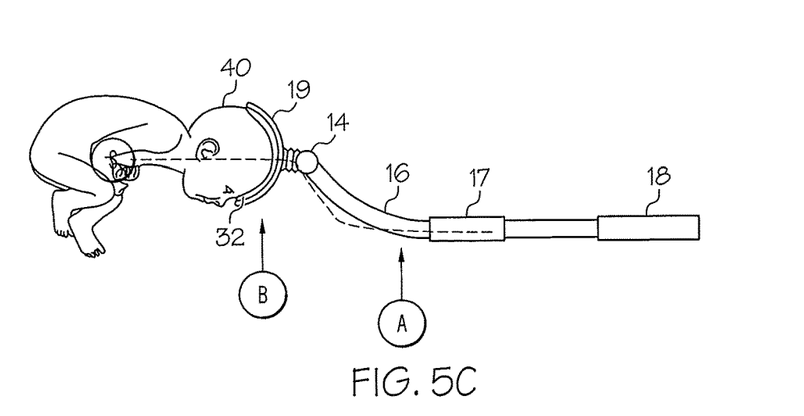

FIGS. 5A-C illustrate the curved "S" route noted above in FIG. 4, with the parturient mother lying supine on a surgical table. Typically a mere 4 to 7 inches in length, this short curved "S" route can be a difficult and tortuous pathway for the fetal head 40 to take back through the birth canal, particularly for an impacted head unable to complete the forward journey. Once the engaging portion 19 is placed adjacent the fetal head 40, the inner cup 32 is inflated by the user and its distal contact surface 33 positioned to make contact with the fetal head 40. As shown in FIG. 5A, the inflated cup 32 can engage the fetal head 40 at position "A". Note that in position "A" the central axis of the pivoting neck 14 is substantially parallel in relation to the lower end of the "S" curve, while the handle 18 is angled upwards. This is due to the curvature of the body portion 16 of the shaft. As the user grasps the handle 18 and directs gentle pressure up the shaft towards the fetal head 40, the applied pressure is transferred along the length of the curved portion 16 to the inflatable cup 32. After shaping and molding the concave surface 33 to the shape of the fetal head, the applied pressure is then directed to and equally distributed along the area making direct contact with the fetal head, which helps disengage the head from its wedged position between the birth canal walls and begin relocation.

Next, as shown in FIG. 5B, the user continues to apply gentle pressure to displace the head 40 back up through the birth canal along curve "S". Here, since the head 40 must now take an upward turn along the slope of curve "S", the handle 18 can be manipulated by the user to change the angle created between the pivoting neck 14 and the engaging portion 19 so that the engaging portion turns upward along the slope of the "S" curve. This in turn adjusts the direction of the applied pressure up the slope of the "S" curve. As the head approaches the top of the "S" slope near position B, as shown in FIG. 5C, the handle 18 can be once again manipulated to turn the pivoting neck 14 and adjust the direction of the applied pressure substantially parallel in relation to the upper end of the "S" curve. Note in FIG. 5C that the body portion 16 is curved to approximate the natural "S" curvature of the parturient woman's birth canal. This serves to prevent resistance to advancement of the shaft within the curved birth canal, and aids in redirecting the applied pressure up the slope of the "S" curve.

Once the fetal head 40 has been satisfactorily relocated as described above, the fetus can be delivered safely via the uterine incision 43, and the inner cup 32 can be deflated for removal from the mother so that the Cesarean section operation can be completed. Deflation of the inner cup allows the engaging portion to be passively compressed by the vaginal walls and assume the compact position 19A (see FIG. 3A) during withdrawal. Deflation can also serve to release any vacuum seal which may have developed with the fetal head. While substantially complete deflation should be done prior to removal, it can be useful to first further inflate the inner cup with an additional amount, e.g. 5-10 cc, of fluid prior to deflating the cup completely, to be sure to sever any vacuum seal with the fetal head. If such a vacuum were to remain during withdrawal of the engaging portion from the birth canal, then the continued vacuum could act to pull the fetal head back down into the birth canal, defeating the purpose of the invention.

When the inventive apparatus is used as described above to gently guide the baby's head through the pelvic curve "S" and into the uterus, there is less resistance to the applied pressure than with other prior art devices. With proper use of the inventive apparatus there are essentially no pressure points placed on the fetal head, as can occur with similar prior art devices or if manual manipulation of the head is attempted, nor are there any gaps in the area of contact with the fetal head. In addition, the pressure gauge can act as a shock absorber to cushion the force applied so that energy/pressure transfer to the fetal head is smooth and gentle. This equal distribution and buffering of applied pressure can substantially eliminate the possibility of causing skull depression, skull fracture or other trauma to the fetal head, and create less chance of a dangerous drop in the fetal heart rate due to an abrupt increase in head pressure.

The inventive apparatus is also advantageous because the contact surface of the inflatable inner cup is manufactured to be contoured to the shape of the fetal head and can be further inflated and deflated after contact to fit the shape of the fetal head and to break any vacuum seal that may have developed with the fetal head prior to removal of the apparatus. The combination of the contoured inflatable cup with a rigid yet curved shaft and a pivoting neck allowing for adjustment of the direction of applied pressure is an improvement over the prior art. The apparatus will appear familiar to obstetricians and other obstetric clinicians, in that it looks similar to and is initially inserted in a similar fashion as a vacuum extractor, which is used for extraction of a non-impacted fetus through the vagina, rather than via C-section.

Materials and Design:

The shaft of the inventive apparatus is preferably a non-collapsible tube made of PVC (polyvinyl chloride), silicone, polyurethane, or any other suitable biocompatible material. The shaft can be between about 200 mm and 2 meters in length, but typically measures approximately 1 meter. The shaft should be formed of a material sufficiently long and rigid so that it can be manipulated into position and transmit an applied force exerted by the user to the fetal head via the engaging portion. The shaft is preferably sufficiently resistant to radial compression (i.e. non-collapsible) so that the lumen remains open along its length, and so that the shaft does not fold or bend while being manipulated by the user.

The pivoting neck can be manufactured to have a full range of vertical and horizontal motion, or with a full range of motion in an up and down direction (i.e. vertical flexion) but with limited or no range of movement in a sideways direction (horizontal flexion). The pivoting neck may be made of any material or structural configuration which can allow vertical and/or horizontal flexion between the shaft and the engaging portion. While not an inclusive list, some examples of a pivoting neck for use with the present invention include a ball and socket type joint (i.e. one which can be snapped together), a ratchet hinge, a detent hinge, a universal joint, or other pivoting connection known in the art.

The outer cup including its rim and inner ridge can be made of flexible, elastic material such as silicone rubber, semi-rigid plastic or other biocompatible elastomer. The Shore A or durometer hardness value of the outer cup is typically larger (i.e. harder, but still flexible) than the inner cup (which is balloon like), but not so large as to make the outer cup as rigid as the shaft. As non-limiting examples, the outer cup can be of soft to medium hardness (35-60 Shore A) and bendable, and the inflatable inner cup can have a 15-25 Shore A hardness. The inflatable inner cup can be blow molded and is generally a thick-walled balloon made of a strong yet deformable material such as PVC, cross-linked polyethylene, or nylon, so that it can mold and conform to the fetal head.

The diameters of the outer cup and inflatable inner cup are comparable to the diameter of the fetal head, typically between about 20 mm and about 100 mm. As noted above, the contact surface of the inner cup, when inflated, has a central concave indentation that is substantially complementary to the shape of a typical vertex of a fetal head, and when properly positioned can be adjusted by inflation/deflation to further shape or mold to match shape of the fetal head. This allows the pressure exerted by the surgeon to be equally distributed along the area of contact between the inflated inner cup and the fetal scalp, thereby substantially eliminating the possibility of causing skull depression, skull fracture or other trauma to the fetal head or neck.

The inner surface of the outer cup and its base can be secured together via a medical adhesive or other biocompatible securing means as is known in the art, e.g., as disclosed in U.S. Pat. No. 8,043,278 to Kelley. Because the inflatable inner cup is typically very deformable in comparison to the outer cup, providing a cushioning base between the outer cup and the inner cup can be useful in a situation where the surgeon is pushing up on the fetal head with such force that the inflated inner cup deforms to the point where the fetal head comes into contact with the base. Having a soft base on the inner surface of the outer cup adds a degree of safety to the inventive apparatus. Also, if a reusable or permanent inflatable inner cup is employed, it can be adhesively secured to the outer cup (e.g. to the rim) and the base by the above referenced means.

The internal lumen of the shaft and the orifice tubing of the inflatable inner cup can have a diameter that is sufficiently large to allow a fluid such as air or saline to flow unrestricted from the proximal opening along the length of the shaft to enter and inflate the inner cup of the engaging portion. For example, the lumen can have a diameter between about 5 mm and about 20 mm, and the shaft can have an outer diameter between about 7 mm and about 25 mm. The areas of the proximal opening and distal opening of the shaft, as well as the orifice tubing of the inner cup, are preferably the same as the cross-sectional area of the internal lumen, but they could be made to be larger or smaller than one another.

The orifice tubing 41 and the inflatable inner cup 32 are preferably of a one-piece construction, but the orifice tubing may also be manufactured as a separate element connecting the inner cup to the distal opening 42 of the lumen. Further, the inflatable inner cup including the orifice tubing can be manufactured to be disposable, such that a new inner cup with its orifice tubing can be placed after each use. Alternatively, the inner cup and orifice tubing can be manufactured to be autoclaved or otherwise sterilized after each use. The orifice tubing, when external to the pivoting neck as shown in FIGS. 2, 3A and 3B, can be enclosed during use by a protective envelope or sheath. As is known in the medical arts, an elongated envelope of flexible plastic sheet material such as polyethylene can be used. Such protective sheaths protect invasive medical devices from abrasion and minimize contact with body cavities and bodily fluids.

While the present invention has been illustrated and described above in considerable detail, it is not intended to restrict or limit the scope of the appended claims to such detail. Additional advantages and modifications will be readily apparent to those skilled in the art without departing from the concept or scope of the invention.

What is claimed is:

1. An obstetric apparatus, comprising:
    a) a substantially rigid and non-collapsible shaft having a proximal end and a distal end, the shaft defining a lumen running longitudinally through the length thereof, the lumen including an opening at the proximal end of the shaft for receiving a fluid, the shaft comprising a handle portion at the proximal end for grasping by a user and a body portion at the distal end, the body portion being curved to approximate the natural curvature of a parturient woman's birth canal;
    b) an engaging portion for engaging the vertex of a fetal head in a parturient woman's birth canal, the engaging portion comprising an outer cup reversibly deformable between a compact position and an expanded position; and an inflatable inner cup for inflation by a user, wherein the inflatable inner cup is in fluid communication with the lumen of the shaft and comprises a distal contact surface including a central concave indentation; and
    c) a pivoting neck connecting the distal end of the shaft to the outer cup and providing a pivoting motion for the engaging portion, wherein the apparatus is useful for repositioning the fetal head towards the uterus,
        wherein the distal contact surface of the inflatable inner cup provides a surface area available for making direct contact with the vertex of the fetal head, and wherein the pressure transferred to the vertex of the fetal head is equally distributed along the surface area during use.

2. The obstetric apparatus of claim 1, further comprising:
d) a pressure gauge for both indicating and buffering the pressure applied to the fetal head.

3. The obstetric apparatus of claim 2, wherein the pressure gauge is located between the handle portion and the body portion of the shaft.

4. The obstetric apparatus of claim 1, wherein the outer cup is biased to assume the expanded position.

5. The obstetric apparatus of claim 1, wherein the outer cup includes a soft base portion for cushioning the fetal head.

6. An obstetric apparatus for repositioning a fetal head wedged in a parturient woman's birth canal, the apparatus comprising:
a) a substantially rigid and non-collapsible shaft having a proximal end and a distal end, the shaft comprising:
   i. a lumen running longitudinally through the length of the shaft, the lumen comprising an opening at the proximal end of the shaft for receiving a fluid;
   ii. a handle portion at the proximal end for grasping by a user;
   iii. a body portion at the distal end, the body portion being curved to approximate the natural curvature of a parturient woman's birth canal; and
   iv. a pressure gauge for both indicating and buffering the pressure applied by the user to a fetal head wedged in the parturient woman's birth canal;
b) an engaging portion for engaging the vertex of the fetal head, the engaging portion comprising:
   i. a flexible outer cup reversibly deformable between a compact position and an expanded position, the outer cup being biased to assume the expanded position; and
   ii. an inflatable inner cup, the inner cup comprising a distal contact surface including a central concave indentation for engaging and molding to the vertex of the head, wherein the inflatable inner cup is in fluid communication with the lumen of the shaft for inflation by the user; and
c) a pivoting neck connecting the distal end of the shaft to the engaging portion and providing a pivoting motion for the engaging portion,
   wherein the distal contact surface of the inflatable inner cup provides a surface area available for making direct contact with the vertex of the fetal head, and wherein the pressure transferred to the vertex of the fetal head is equally distributed along the surface area during use.

7. The obstetric apparatus of claim 6, wherein the pressure gauge is located between the handle portion and the body portion of the shaft.

8. The obstetric apparatus of claim 6, wherein the outer cup includes a soft base portion for cushioning the fetal head.

9. A method of repositioning the head of a fetus within a parturient woman's birth canal, the method comprising the steps of:
a) inserting an obstetric apparatus into the birth canal of a parturient woman, the obstetric apparatus comprising:
   i. a substantially rigid and non-collapsible shaft having a proximal end and a distal end, the shaft defining a lumen running longitudinally through the length thereof, the lumen including an opening at the proximal end of the shaft for receiving a fluid, the shaft comprising a handle portion at the proximal end for grasping by a user and a curved body portion at the distal end;
   ii. an engaging portion for engaging the vertex of a fetal head located in the birth canal, the engaging portion comprising an outer cup and an inflatable inner cup, the inner cup in fluid communication with the lumen of the shaft and comprising a contact surface including a central concave indentation for engaging and molding to the vertex of the fetal head; and
   iii. a pivoting neck connecting the shalt to the outer cup and providing a pivoting motion for the engaging portion, wherein the distal contact surface of the inflatable inner cup provides a surface area available for making direct contact with the vertex of the fetal head, and wherein the pressure transferred to the vertex of the fetal head is equally distributed along the surface area during use;
b) positioning the engaging portion of the obstetric apparatus adjacent the vertex of the fetal head;
c) injecting fluid into the opening at the proximal end of the shaft to inflate the inflatable inner cup of the engaging portion;
d) applying pressure along the shaft so that the contact surface of the inflatable inner cup engages the vertex of the fetal head and transfers the applied pressure to the fetal head; and
e) maneuvering the shaft to reposition the fetal head towards the uterus of the parturient woman.

10. The method of claim 9, further comprising the step of:
f) adjustably inflating or deflating the inner cup to mold the contact surface of the inflatable inner cup to the shape of the engaged fetal head, wherein this step is performed any time following step (d) of applying pressure along the shaft.

11. The method of claim 9, further comprising the steps of:
g) prior to removal, deflating the inflatable inner cup to release any vacuum seal created between the inner cup and the fetal head; and
h) removing the apparatus from the birth canal, wherein steps (g) and (h) are performed following completion of step (e) of maneuvering the shaft to reposition the fetal head towards the uterus of the parturient woman.

12. The method of claim 11, wherein step (g) includes further inflating the inflatable inner cup prior to deflating the inflatable inner cup.

* * * * *